United States Patent
Drobnik et al.

(10) Patent No.: US 7,199,375 B2
(45) Date of Patent: Apr. 3, 2007

(54) RADIATION SHIELDING CONTAINER THAT ENCLOSES A VIAL OF ONE OR MORE RADIOACTIVE SEEDS

(75) Inventors: Christopher D. Drobnik, Wauconda, IL (US); Michael W. Drobnik, Downers Grove, IL (US)

(73) Assignee: Bard Brachytherapy, Inc., Carol Stream, IL (US)

( * ) Notice: Subject to any disclaimer, the term of this patent is extended or adjusted under 35 U.S.C. 154(b) by 88 days.

(21) Appl. No.: 10/963,382

(22) Filed: Oct. 12, 2004

(65) Prior Publication Data

US 2006/0076520 A1   Apr. 13, 2006

(51) Int. Cl.
  *A61M 36/00*  (2006.01)
  *A61N 5/00*  (2006.01)
  *H01J 37/20*  (2006.01)
(52) U.S. Cl. ............ 250/455.11; 600/7; 600/1
(58) Field of Classification Search ........... 250/455.11, 250/453.11; 600/7.1
  See application file for complete search history.

(56) References Cited

U.S. PATENT DOCUMENTS

| | | | |
|---|---|---|---|
| 1,576,535 A | 3/1926 | Muir | |
| 2,915,640 A | 12/1959 | Grubel et al. | |
| 3,256,441 A | 6/1966 | Grasly | |
| 3,369,121 A | 2/1968 | Bruno et al. | |
| 3,770,964 A | 11/1973 | Backus | |
| 3,882,315 A | 5/1975 | Soldan | |
| 4,020,355 A | 4/1977 | Czaplinski et al. | |
| 4,081,688 A | 3/1978 | Fries | |
| 4,501,360 A | 2/1985 | Levy et al. | |
| 4,509,506 A * | 4/1985 | Windorski et al. ........... | 600/8 |
| 4,535,250 A | 8/1985 | Fields | |
| 4,626,402 A | 12/1986 | Baatz et al. | |
| 4,673,813 A | 6/1987 | Sanchez | |
| 4,752,437 A | 6/1988 | Ito et al. | |
| 4,759,345 A | 7/1988 | Mistry | |
| 4,783,309 A | 11/1988 | Popp et al. | |
| 4,788,438 A | 11/1988 | Evers | |
| 4,836,975 A | 6/1989 | Guldner et al. | |
| 4,846,235 A | 7/1989 | Handke | |

(Continued)

FOREIGN PATENT DOCUMENTS

DE   3516838   11/1986

(Continued)

OTHER PUBLICATIONS

U.S. Appl. No. 10/642,048.

*Primary Examiner*—Nikita Wells
*Assistant Examiner*—Johnnie L Smith, II
(74) *Attorney, Agent, or Firm*—Carmen B. Patti & Associates LLC (57) ABSTRACT

An apparatus in one example comprises a vial that comprises a vial bottom and a vial cap that connect to enclose one or more radioactive seeds; and a radiation shielding container that comprises a bottom portion and a top portion that connect to enclose the vial. The radiation shielding container and the vial comprise one or more vents for movement of a sterilant therethrough for sterilization of the one or more radioactive seeds within the vial. The bottom portion of the radiation shielding container comprises a structure that engages the vial bottom to prevent rotational movement of the vial bottom during removal of the vial cap.

30 Claims, 5 Drawing Sheets

U.S. PATENT DOCUMENTS

| | | | |
|---|---|---|---|
| 4,847,505 A | 7/1989 | Suthanthiran | |
| 4,863,023 A | 9/1989 | Payne et al. | |
| 4,872,563 A | 10/1989 | Warder et al. | |
| 4,920,270 A * | 4/1990 | Grodzins | 250/364 |
| 4,923,088 A | 5/1990 | Tanaka et al. | |
| 4,968,305 A | 11/1990 | Takahashi et al. | |
| 4,972,087 A | 11/1990 | Neider et al. | |
| 4,994,012 A | 2/1991 | Nakayama et al. | |
| 4,997,090 A | 3/1991 | Lenmark, Sr. et al. | |
| 5,102,615 A | 4/1992 | Grande et al. | |
| 5,274,239 A | 12/1993 | Lane et al. | |
| 5,303,836 A | 4/1994 | Childress | |
| 5,346,096 A | 9/1994 | Diersch et al. | |
| 5,397,902 A * | 3/1995 | Castner et al. | 250/432 PD |
| 5,460,592 A | 10/1995 | Langton et al. | |
| 5,475,721 A | 12/1995 | Baatz et al. | |
| 5,519,931 A | 5/1996 | Reich | |
| 5,536,945 A | 7/1996 | Reich | |
| 5,552,612 A | 9/1996 | Katayama et al. | |
| 5,672,883 A | 9/1997 | Reich | |
| 5,716,317 A | 2/1998 | Okano et al. | |
| 5,752,603 A * | 5/1998 | Faber | 206/530 |
| 5,828,073 A | 10/1998 | Zhu et al. | |
| 5,829,594 A | 11/1998 | Warder | |
| 5,831,271 A | 11/1998 | Okano et al. | |
| 5,834,788 A * | 11/1998 | Fu et al. | 250/506.1 |
| 5,894,134 A | 4/1999 | Kissinger | |
| 5,944,190 A | 8/1999 | Edelen | |
| 5,949,084 A | 9/1999 | Schwartz | |
| RE36,693 E | 5/2000 | Reich | |
| 6,064,710 A | 5/2000 | Singh | |
| 6,084,243 A | 7/2000 | Smith, Jr. et al. | |
| 6,106,455 A | 8/2000 | Kan | |
| 6,108,392 A | 8/2000 | Yoshizawa et al. | |
| 6,113,529 A | 9/2000 | Shi | |
| 6,114,710 A | 9/2000 | Contrepois et al. | |
| 6,155,420 A | 12/2000 | Phillips | |
| 6,166,284 A | 12/2000 | Oelsner | |
| 6,195,404 B1 | 2/2001 | Lemogne et al. | |
| 6,256,363 B1 | 7/2001 | Methling et al. | |
| 6,323,501 B1 | 11/2001 | White et al. | |
| 6,366,633 B1 | 4/2002 | Stezaly et al. | |
| 6,372,157 B1 | 4/2002 | Krill, Jr. et al. | |
| 6,425,174 B1 | 7/2002 | Reich | |
| 6,438,190 B2 | 8/2002 | Gluschke et al. | |
| 6,452,200 B1 | 9/2002 | Kotler | |
| 6,472,675 B2 | 10/2002 | White et al. | |
| 6,489,623 B1 | 12/2002 | Peters et al. | |
| 6,494,824 B1 | 12/2002 | Apple et al. | |
| 6,498,826 B2 | 12/2002 | Gluschke et al. | |
| 6,530,875 B1 | 3/2003 | Taylor et al. | |
| 6,531,705 B2 | 3/2003 | White et al. | |
| 6,538,259 B2 | 3/2003 | Matsunaga et al. | |
| 6,576,918 B1 | 6/2003 | Fu et al. | |
| 6,586,758 B2 | 7/2003 | Martin | |
| 6,614,040 B1 | 9/2003 | Zens | |
| 6,632,176 B2 | 10/2003 | McIntire et al. | |
| 6,639,236 B1 | 10/2003 | Low et al. | |
| 6,639,237 B2 | 10/2003 | Pedersen et al. | |
| 6,649,922 B1 | 11/2003 | McKenzie | |
| 6,664,555 B2 | 12/2003 | White et al. | |
| 6,665,365 B2 | 12/2003 | Dallongeville et al. | |
| 6,689,043 B1 | 2/2004 | McIntire et al. | |
| 6,692,426 B1 * | 2/2004 | Faulkner et al. | 600/8 |
| 6,699,439 B1 | 3/2004 | Dannert et al. | |
| 6,717,163 B2 | 4/2004 | Zens | |
| 6,722,499 B2 | 4/2004 | Reich | |
| 6,727,510 B2 | 4/2004 | Matsunaga et al. | |
| 6,749,553 B2 | 6/2004 | Brauckman et al. | |
| 6,802,828 B2 * | 10/2004 | Reynolds | 604/199 |
| 6,989,543 B2 * | 1/2006 | Drobnik et al. | 250/455.11 |
| 2001/0015989 A1 | 8/2001 | Gluschke et al. | |
| 2001/0032851 A1 | 10/2001 | Pennington et al. | |
| 2002/0178566 A1 * | 12/2002 | Reich | 29/426.5 |
| 2003/0028068 A1 | 2/2003 | Steele et al. | |
| 2003/0088143 A1 | 5/2003 | Pedersen et al. | |
| 2003/0146399 A1 | 8/2003 | Martin et al. | |
| 2003/0171639 A1 | 9/2003 | Taylor et al. | |
| 2003/0222228 A1 | 12/2003 | Chen et al. | |
| 2004/0015038 A1 | 1/2004 | Lemer | |
| 2004/0016098 A1 * | 1/2004 | Reich | 29/428 |
| 2004/0047444 A1 | 3/2004 | White et al. | |
| 2004/0097779 A1 | 5/2004 | McIntire et al. | |

FOREIGN PATENT DOCUMENTS

| | | |
|---|---|---|
| DE | 4004037 | 5/1991 |
| EP | 0049439 | 4/1982 |
| EP | 0091175 | 10/1983 |
| EP | 0405241 | 1/1991 |
| EP | 1076340 | 2/2001 |
| GB | 2024694 | 1/1980 |
| GB | 2163084 | 2/1986 |
| JP | 2264900 | 10/1990 |
| JP | 3099744 | 4/1991 |

* cited by examiner

RADIATION SHIELDING CONTAINER THAT ENCLOSES A VIAL OF ONE OR MORE RADIOACTIVE SEEDS

CROSS-REFERENCE TO RELATED APPLICATION

This application contains subject matter that is related to the subject matter of the following application, which is assigned to the same assignee as this application. The below-listed application is hereby incorporated herein by reference in its entirety.

"RADIATION SHIELDING CONTAINER FOR RADIOACTIVE SOURCES," by Drobnik, et al., Ser. No. 10/642,048, filed Aug. 15, 2003.

TECHNICAL FIELD

The invention relates generally to shielding containers and more particularly to radiation shielding containers for radioactive sources.

BACKGROUND

Bodily cancers are commonly treated using radiation therapy. Radiation therapy employs high energy radiation to kill cancer cells. One type of radiation therapy is brachytherapy, in which a source of radiation is in direct contact with an afflicted tissue. A common brachytherapy treatment, transperineal seed implantation, involves placing radioactive seeds in the prostate gland to kill prostate gland cancer cells. A physician employs tools, for example, ultrasound, computerized axial tomography ("CAT") scans, and X-ray images in concert with dose-planning computer software programs to evaluate the medical condition of a patient. The physician constructs an optimal treatment plan to evenly distribute radiation throughout the afflicted tissue. Radioactive seeds of discrete radioactive strengths are inserted into the afflicted tissue through multiple implantation needles at positions corresponding to the treatment plan.

The physician in one example employs a radioactive seed applicator to insert the radioactive seeds into the afflicted tissue. The physician receives the radioactive seeds in a radiation shielding container and loads the radioactive seeds into the radioactive seed applicator. The radiation shielding container in one example is made from lead or steel to shield the physician from radiation of the radioactive seeds. The physician in one example opens the radiation shielding container and removes the radioactive seeds for placement into an autoclave for sterilization. The physician may not be shielded from the radioactive seeds during the time period between removing the radioactive seeds from the radiation shielding container and placing the radioactive seeds in the autoclave. As one shortcoming, the physician is exposed to radiation from the radioactive seeds during sterilization of the radioactive seeds.

Thus, a need exists for a radiation shielding container that promotes a reduction in exposure to radiation by a physician while handling radioactive seeds.

SUMMARY

The invention in one implementation encompasses an apparatus. The apparatus comprises: a vial that comprises a vial bottom and a vial cap that connect to enclose one or more radioactive seeds; and a radiation shielding container that comprises a bottom portion and a top portion that connect to enclose the vial. The radiation shielding container and the vial comprise one or more vents for movement of a sterilant therethrough for sterilization of the one or more radioactive seeds within the vial. The bottom portion of the radiation shielding container comprises a structure that engages the vial bottom to prevent rotational movement of the vial bottom during removal of the vial cap.

Another implementation of the invention encompasses an apparatus. The apparatus comprises: a vial that comprises a vial bottom and a vial cap that connect to enclose one or more radioactive seeds; and a radiation shielding container that comprises a bottom portion and a top portion that connect to enclose the vial. The radiation shielding container comprises one or more tortuous paths that allow passage of a sterilant and prevent passage of radiation from the one or more radioactive seeds. The vial comprises a sterile barrier that allows passage of the sterilant into the vial for sterilization of the one or more radioactive seeds within the vial. The bottom portion of the radiation shielding container comprises a structure that engages the vial bottom to prevent rotational movement of the vial bottom during removal of the vial cap.

Yet another implementation of the invention encompasses an apparatus. The apparatus comprises: a vial that comprises a vial bottom and a vial cap that connect to enclose one or more radioactive seeds; means for housing the vial that shields a user from radiation emitted by the one or more radioactive seeds; means for allowing passage of a sterilant into the means for housing; means for allowing passage of the sterilant into the vial for sterilization of the one or more radioactive seeds within the vial; and means for engaging the vial bottom to prevent rotational movement of the vial bottom during removal of the vial cap.

DESCRIPTION OF THE DRAWINGS

Features of exemplary implementations of the invention will become apparent from the description, the claims, and the accompanying drawings in which:

DETAILED DESCRIPTION

Figure 1:
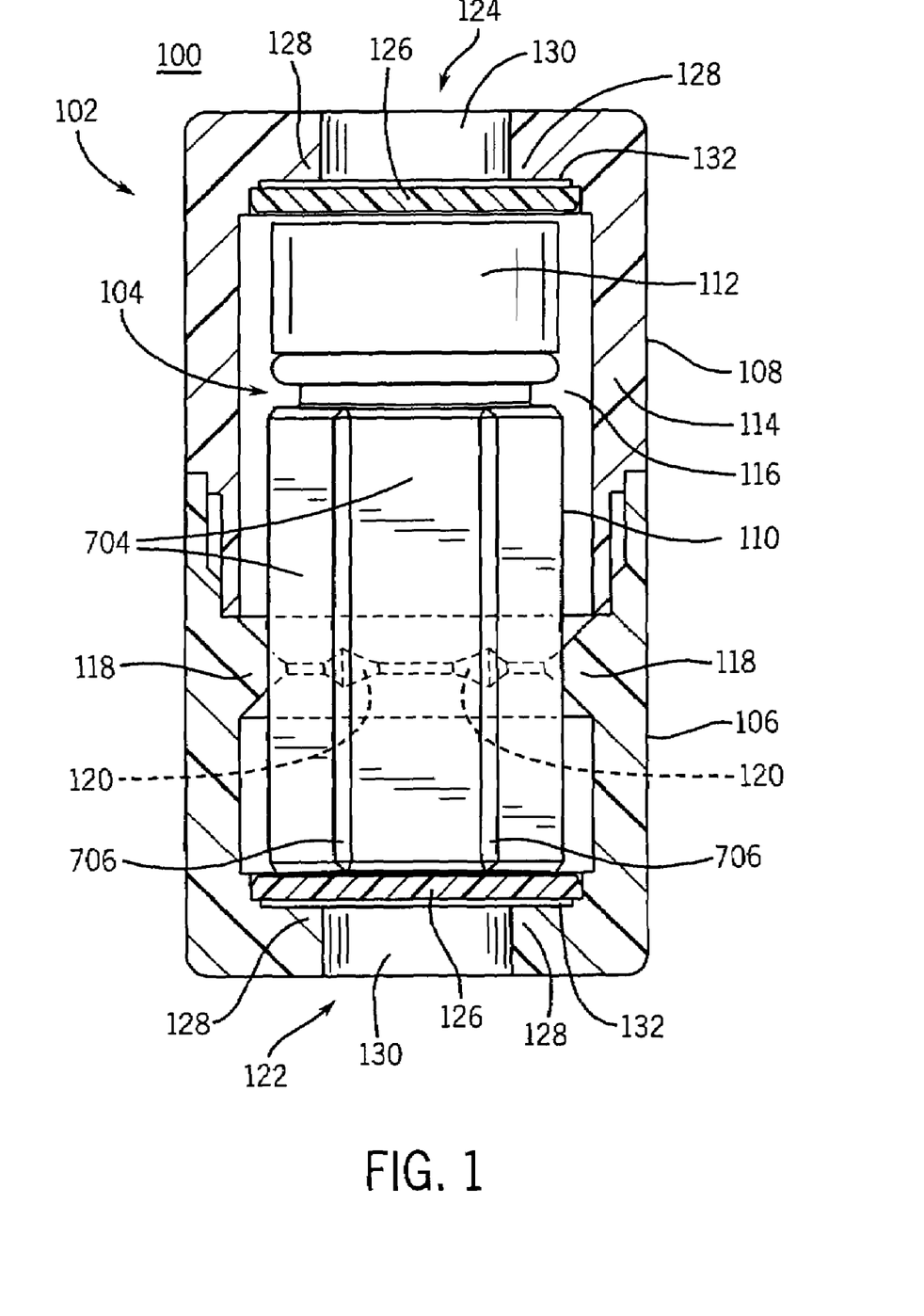
FIG. 1 is a representation of an exemplary implementation of an apparatus that comprises a radiation shielding container that encloses a vial.

Turning to FIG. 1, an apparatus 100 comprises a radiation shielding container 102 and a vial 104. The radiation shielding container 102 comprises a bottom portion 106 and a top portion 108 that connect to enclose the vial 104. The vial 104 comprises a vial bottom 110 and a vial cap 112 that connect to enclose one or more radioactive sources. The radioactive sources in one example comprise radioactive seeds for use in brachytherapy treatments.

The radiation shielding container 102 in one example comprises a stainless steel container for shipping and/or storage of the radioactive seeds. The radiation shielding container 102 in one example comprises a radiation resistant shell 114 and an internal chamber 116. The radiation resistant shell 114 shields an outer surface of the radiation shielding container 102 from radiation of the radioactive seeds that are within the internal chamber 116. For example, the radiation resistant shell 114 shields a user of the radiation shielding container 102 from a portion of the radiation emitted from the radioactive seeds.

The radiation resistant shell 114 comprises a radiation shielding metal, for example, stainless steel. Stainless steel may be readily disposed or reused. For example, stainless steel can be disposed with normal trash rather than as chemical waste. The radiation resistant shell 114 comprises a thickness that is sufficient to shield a user of the radiation shielding container 102 from radiation of the radioactive seeds that are stored within the internal chamber 116. For example, the thickness of the radiation resistant shell 114 is sufficient to shield nuclides of the radioactive seeds used in brachytherapy, for example, Iodine-125 ("I-125") or Palladium-103 ("Pd-103"). The thickness of the radiation resistant shell 114 in one example is about three or four millimeters (⅛ inch).

Referring to FIGS. 1–6, the bottom portion 106 and the top portion 108 of the radiation shielding container 102 engage to enclose the vial 104 within the internal chamber 116. In one example, the top portion 108 comprises a cover to the bottom portion 106. For example, the top portion 108 comprises a lid to enclose the vial 104 in the internal chamber 116 within the bottom portion 106. In another example, the bottom portion 106 comprises a bottom half portion and the top portion 108 comprises a top half portion. For example, the bottom portion 106 and the top portion 108 comprise a substantially similar size.

Figure 4:
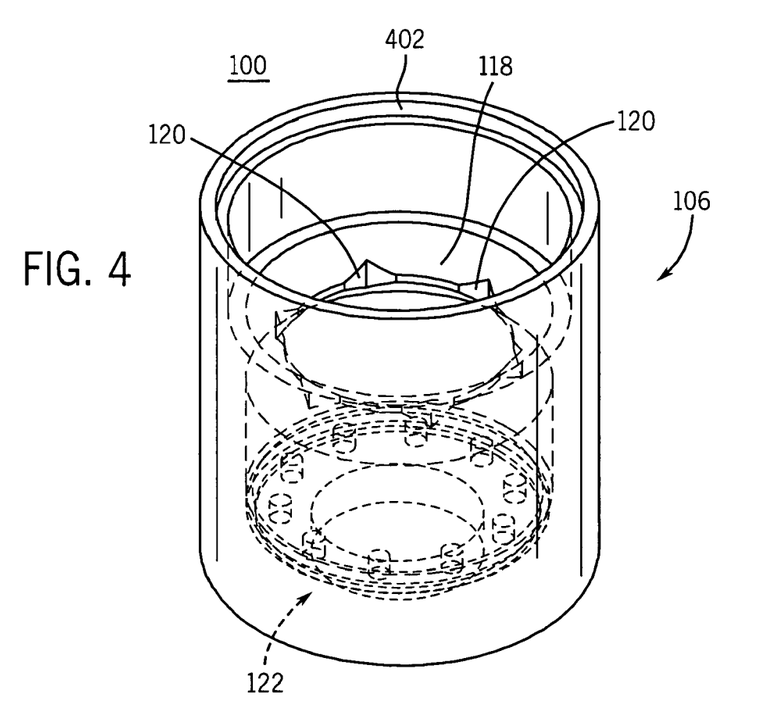
FIG. 4 is a perspective representation of the bottom portion of the apparatus of FIG. 3.
Figure 5:
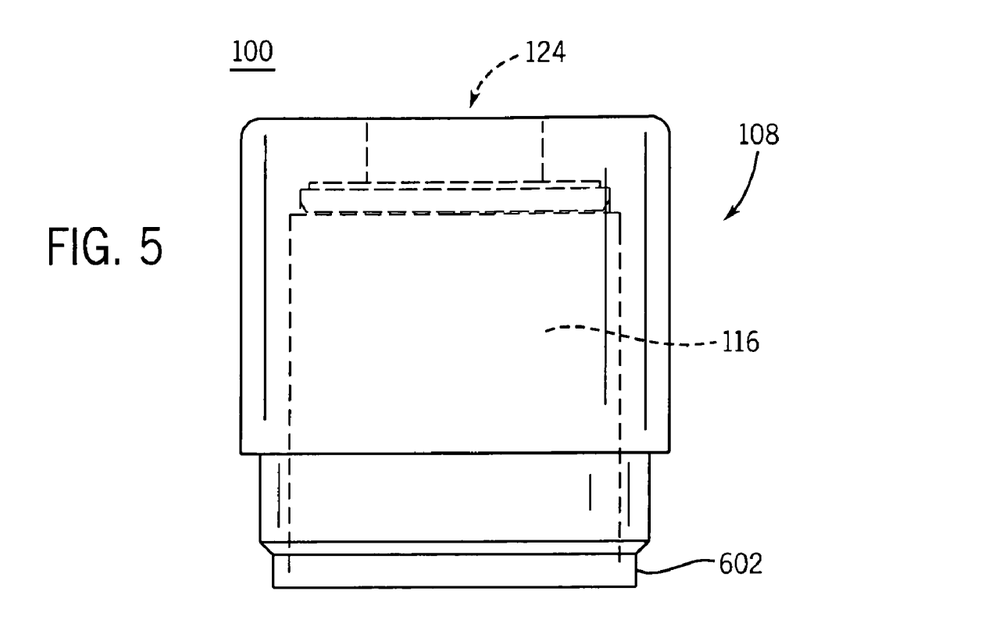
FIG. 5 is a representation of a top portion of the radiation shielding container of the apparatus of FIG. 1.
Figure 6:
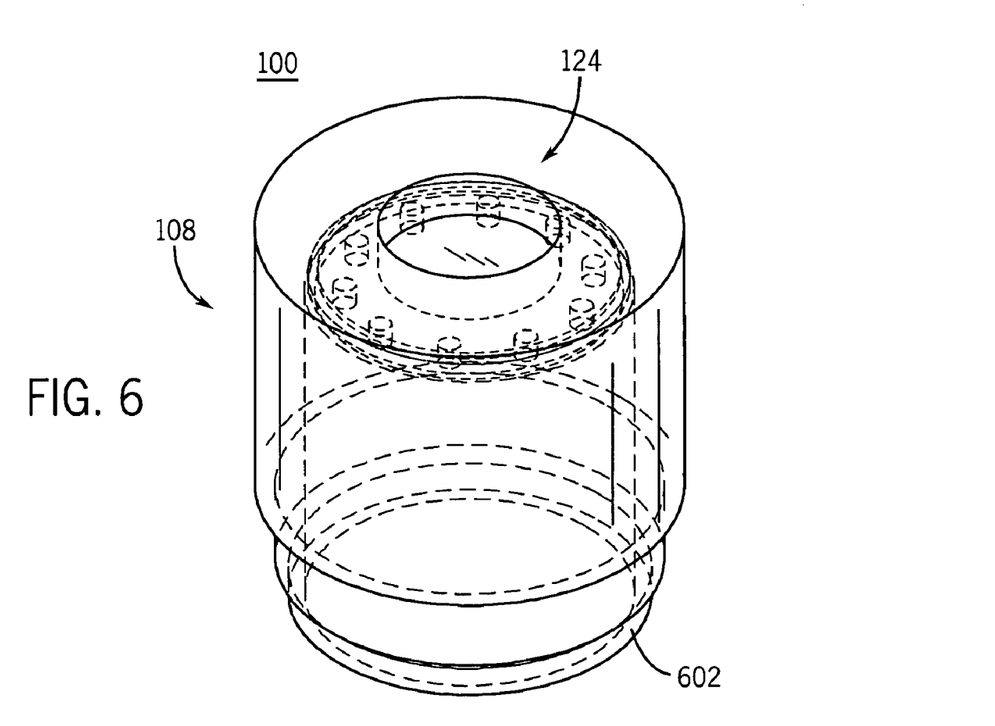
FIG. 6 is a perspective representation of the top portion of the apparatus of FIG. 5.

Referring to FIGS. 1, 4, and 6, the bottom portion 106 and the top portion 108 employ a connection component to couple the bottom portion 106 with the top portion 108. For example, the connection component may be a bayonet connection, a screw cap connection, or a threaded connection. In one example, the bottom portion 110 comprises a first threaded connection portion 402 and the top portion 108 comprises a second threaded connection portion 602. The first threaded connection portion 402 and the second threaded connection portion 602 engage to enclose the vial 104 within the radiation shielding container 102. For example, the first threaded connection portion 402 and the second threaded connection portion 602 screw together to connect the bottom portion 106 together with the top portion 108.

Referring to FIG. 1, the radiation shielding container 102 may also be used for sterilization of the radioactive seeds within the vial 104. For example, the radiation shielding container 102 may be used for sterilization of the radioactive seeds by passing sterilants into the radiation shielding container 102. For example, the sterilants may comprise steam, hydrogen peroxide, ethylene oxide, and/or gamma rays.

The radiation shielding container 102 comprises one or more vents 122 and 124. The vents 122 and 124 allow passage of a sterilant through the radiation shielding container 102. The sterilant in one example comprises a sterilization gas, such as steam. For example, the vents 122 and 124 allow passage of the steam through the internal chamber 116 for sterilization of the radioactive seeds within the vial 104. The vents 122 and 124 allow sterilization of the radioactive seeds while the vial 104 is enclosed within the radiation shielding container 102. Since the vents 122 and 124 allow the contents of the radiation shielding container 102 to be sterilized without opening the radiation shielding container 102, the vents 122 and 124 serve to help prevent spillage of the contents of the radiation shielding container 102.

The radiation resistant shell 114 comprises one or more passages that form the vents 122 and 124. The passages cause the sterilant to follow one or more tortuous paths between the internal chamber 116 and the exterior of the radiation shielding container 102. The vent 122 in one example comprises a tortuous path through the bottom portion 106. The vent 124 in one example comprises a tortuous path through the top portion 108.

The tortuous paths through the bottom and top portions 106 and 108 allow the passage of the sterilant into and out of the internal chamber 116. For example, one or more of the tortuous paths allow an entrance of the sterilant into the radiation shielding container 102 and one or more of the tortuous paths allow an exit of the sterilant from the radiation shielding container 102. However, the tortuous paths prevent radiation of the radioactive seeds from passing out the vents 122 and 124. For example, the tortuous paths through the bottom and top portions 106 and 108 are not direct line of sight paths for the radiation. The vents 122 and 124 comprise indirect paths comprising one or more bends or turns. The vents 122 and 124 serve to prevent a direct line of sight between the radioactive sources 202 and a user of the radiation shielding container 102. The tortuous paths through the bottom and top portions 106 and 108 also prevent passage a radioactive seed from the internal chamber 116. For example, the size and shape of the openings in the vents 122 and 124 prevents exit of a common radioactive seed used in brachytherapy.

The vent 122 in one example is substantially similar to the vent 124. For example, the vents 122 and 124 each comprise a radiation resistant disk 126, a lip 128 of the radiation resistant shell 114, an opening 130 in the radiation resistant shell 104, and a space 132 between the radiation resistant disk 126 and the lip 128. The radiation resistant disk 126 is connected to the radiation resistant shell 114 at a position to leave the space 132 between the radiation resistant disk 126 and the lip 128.

Figure 2:
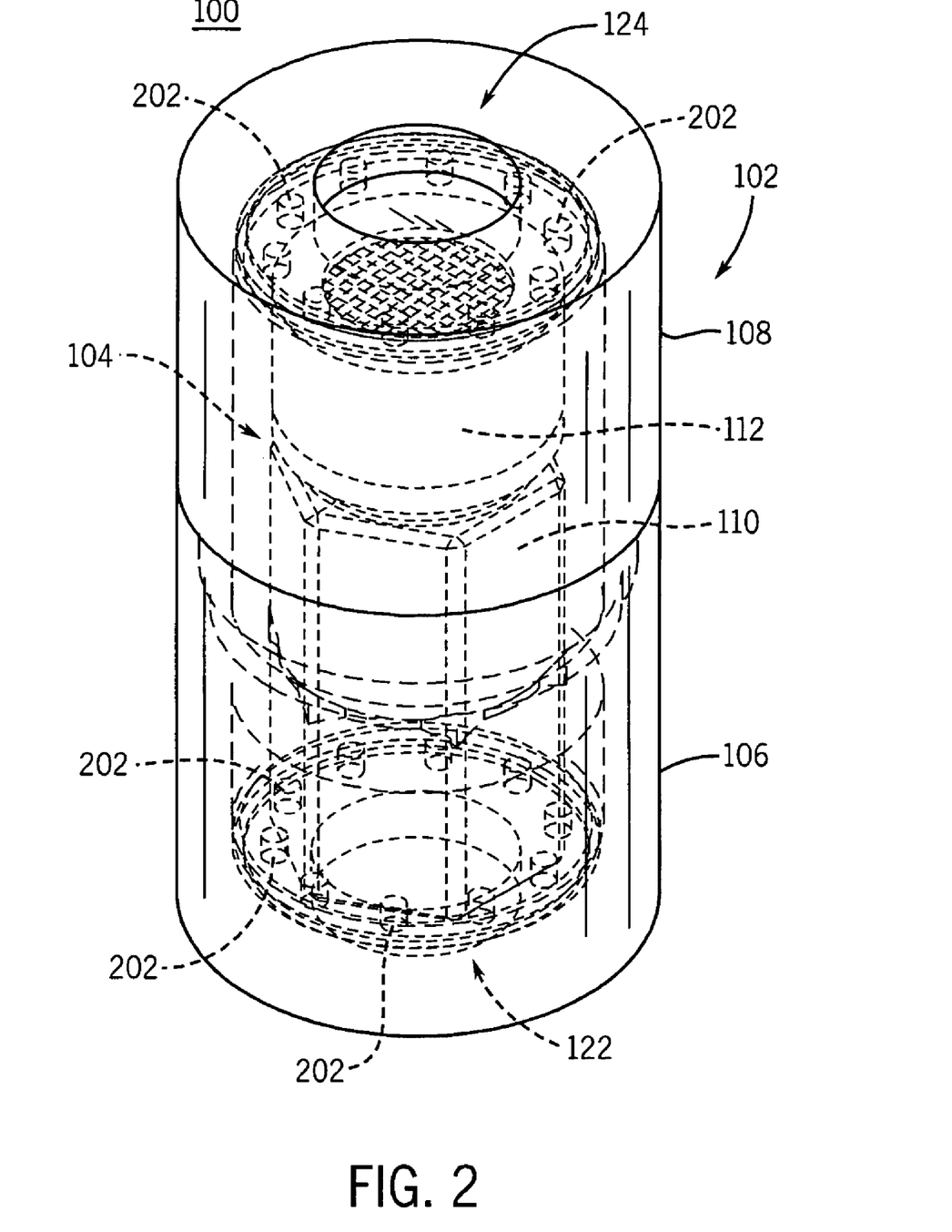
FIG. 2 is a perspective representation of the radiation shielding container and the vial of the apparatus of FIG. 1.
Figure 3:
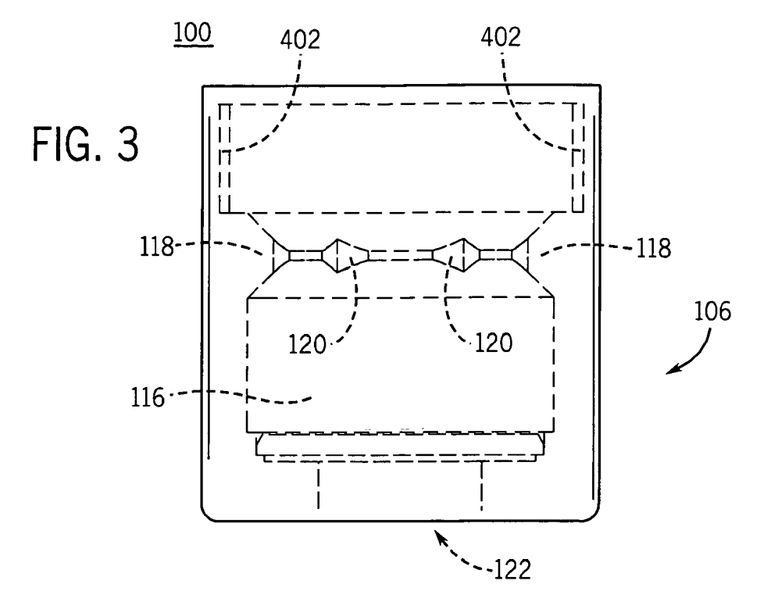
FIG. 3 is a representation of a bottom portion of the radiation shielding container of the apparatus of FIG. 1.

Referring to FIGS. 1–2, the radiation resistant disk 126 comprises one or more holes 202. The holes 202 are aligned to be concealed under the lip 128 of the radiation resistant shell 114. For example, the sterilant may pass through the holes 202, but does not have a direct line of sight path into or out of the internal chamber 116. Therefore, the vent 122 prevents the passage of radiation from the radioactive seeds.

In one example, the vent 122 allows passage of the sterilant into the internal chamber 116. The sterilant is able to pass through the opening 130 in the radiation resistant shell 114 into the space 132. The sterilant then is able to pass around the lip 128 from the opening 130 to the space 132 under the lip 128. The sterilant is then able to pass through the holes 202 in the radiation resistant disk 126 and into the internal chamber 116.

In another example, the vent 122 allows passage of the sterilant out of the internal chamber 116. The sterilant is able to pass from the internal chamber 116 through the holes 202 in the radiation resistant disk 126 and into the space 132 under the lip 128. The sterilant then is able to pass around the lip 128 from the space 132 to the opening 130 in the radiation resistant shell 114. The sterilant is then released outside of the radiation shielding container 102.

Figure 7:
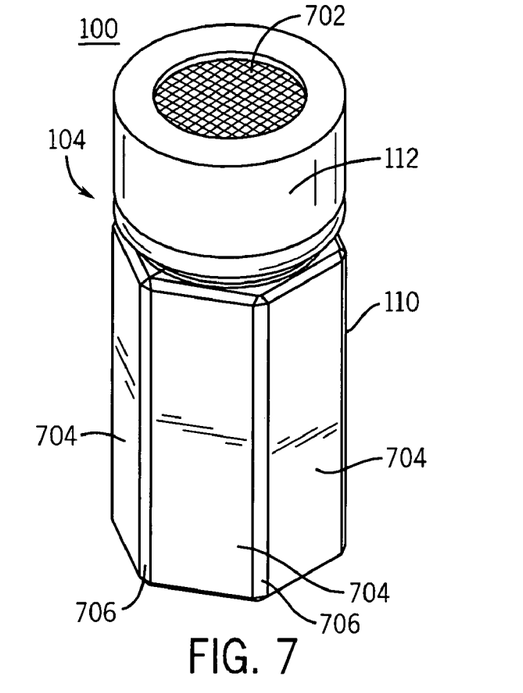
FIG. 7 is a perspective representation of the vial of the apparatus of FIG. 1.

Referring to FIG. 7, the vial 104 is made of a material that can be autoclaved and still maintain structural integrity. For example, the vial 104 may comprise polycarbonate, anti-static plastic, or glass. The vial 104 comprises one or more vents for movement of a sterilant therethrough for sterilization of the radioactive seeds within the vial 104. For example, the vial cap 112 comprises a sterile barrier 702 that allows passage of the sterilant into the vial 104. The sterile barrier 702 allows passage of a sterilant, but prevents passage of microbes. Therefore, after sterilization of the radioactive seeds within the vial 104, the sterile barrier 702 maintains the sterility of the radioactive seeds. Since the sterile barrier 702 allows the radioactive seeds within the vial 104 to be sterilized without opening the vial 104, the sterile barrier 702 serves to help prevent spillage of the radioactive seeds from the vial 104. The sterile barrier 702 in one example comprises a vent material offered by W. L. Gore & Associates, Inc. (555 Papermill Road, Newark, Del. 19711), under the trade identifier Gore-Tex®.

Figure 8:
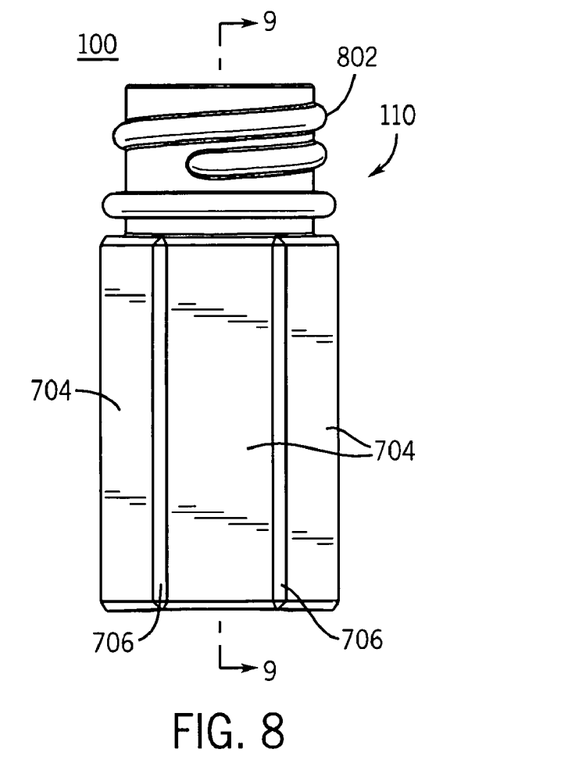
FIG. 8 is a representation of a vial bottom of the vial of FIG. 7.

Referring to FIGS. 7 and 8, the vial bottom 110 comprises a connection portion 802. In one example, the connection portion 802 comprises a threaded connection. In another example, the connection portion 802 comprises a bayonet closure. The vial cap 112 comprises a mating connection portion (not shown) to engage with the connection portion 802 to secure the vial cap 112 to the vial bottom 110. For example, the vial cap 112 may comprise a threaded connection that mates with the threaded connection portion 802. The vial cap 112 is rotationally removable from the vial bottom 110.

Figure 9:
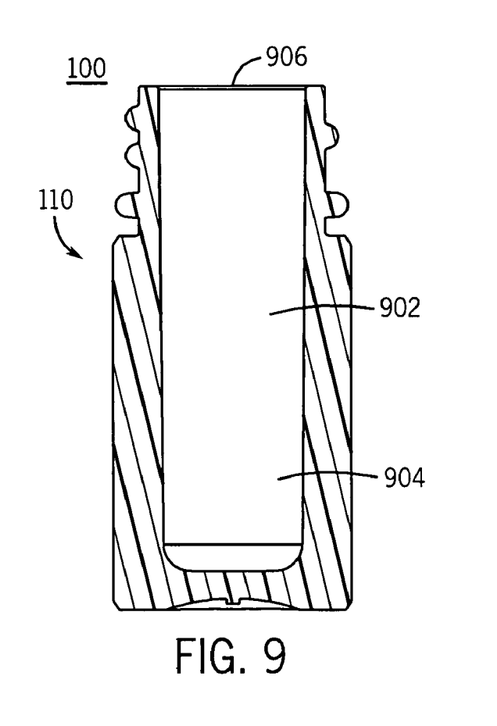
FIG. 9 is a sectional representation of the vial bottom directed along line 9—9 of FIG. 8.

Referring to FIG. 9, the vial bottom 110 comprises an inner chamber 902. The inner chamber in one example comprises a prism shape, such as a circle, square, or hexagon based prism. The inner chamber 902 comprises a substantially uniform cross-section from a bottom portion 904 of the inner chamber 902 to an opening 906 of the inner chamber 902. The inner chamber in one example comprises a cylindrical shape. The opening 906 of the inner chamber 902 in one example comprises a substantially same diameter as the bottom portion 904 of the inner chamber 902. For example, the diameter of the inner chamber 902 is substantially uniform from the bottom 904 of the inner chamber 902 to the opening 906 of the inner chamber 902. The radius of the inner chamber 902 is substantially uniform to promote accessibility of the radioactive seeds within the inner chamber 902 from the opening 906.

Referring to FIG. 7, the vial bottom 110 comprises a plurality of outer faces 704. In one example, the vial bottom 110 comprises a square shape with four outer faces. In another example, the vial bottom 110 comprises a hexagonal shape with six outer faces. The vial bottom 110 comprises corners 706 between the outer faces 704. For example, the hexagonal shaped vial bottom 110 has six corners. In yet another example, the outer faces 704 comprise additional rotation restriction features to prevent rotation of the vial bottom 110 in the bottom portion 106 of the radiation shielding container 102.

Referring to FIGS. 1 and 7, the bottom portion 106 of the radiation shielding container 102 comprises a structure that engages the vial bottom 110. In one example, the structure comprises a recess in the bottom portion 106 that restricts rotation of the vial bottom 110. In another example, the structure comprises a circumferential protrusion 118 with a plurality of notches 120. The circumferential protrusion 118 in one example is integral with or press fit into the bottom portion 106 of the radiation shielding container 102. The circumferential protrusion 118 extends into the internal chamber 116 from an inner surface of the radiation resistant shell 114. The notches 120 are sized and positioned around the circumferential protrusion 118 to receive the corners 706 of the vial bottom 110.

Upon placement of the vial 104 into the bottom portion 106 of the radiation shielding container 102, the notches 120 receive the vial bottom 110 and abut the outer faces 704 and/or corners 706 of the vial bottom 120. In one example, the outer surface of the vial bottom 110 comprises a hexagonal prism shape with six outer faces 704 and six corners 706. The corresponding circumferential protrusion 118 comprises six notches 120 positioned around the length of the circumferential protrusion 118 to align with the six corners 706 of the vial bottom 110. In another example, the outer surface of the vial bottom 110 comprises a square prism shape with four outer faces 704 and four corners 706. The corresponding circumferential protrusion 118 comprises four notches 120 positioned around the length of the circumferential protrusion 118 to align with the four corners 706 of the vial bottom 110. Alternatively, the circumferential protrusion 118 may comprise any number of notches 120 to align with the outer surface of a vial bottom 110 of another shape with another number of corners 706.

The circumferential protrusion 118 and notches 120 engage with the vial bottom 110 to prevent rotational movement of the vial bottom during rotational removal of the vial cap 112. For example, a user applies a rotational force to the vial cap 112 to remove the vial cap from the vial bottom 110. The abutment between the notches 120 and the outer faces 704 of the vial bottom 110 prevents rotational movement of the vial bottom 110 while the user removes the vial cap 112. Since the circumferential protrusion 118 and notches 120 prevent a rotational force applied to the vial cap 112 from translating into rotational movement of the vial bottom 110, the vial bottom 110 may remain within the bottom portion 106 of the radiation shielding container 102 during removal of the vial cap 112. The user does not need to remove the vial 104 from the bottom portion 106 and hold the vial bottom 110 while rotationally removing the vial cap 112. Therefore, the bottom portion 106 of the radiation shielding container 102 shields the user from a portion of the radiation emitted by the radioactive seeds within the vial 104 while the user removes the vial cap 112.

Referring to FIG. 1, the radiation shielding container 102 in one example comprises a shipping container for radioactive seeds. The radiation shielding container 102 may be sterilized before and/or after shipment. For example, the radiation shielding container 102 may be autoclaved at a first location, sealed in a sterile bag, and shipped to a second location. The sterile bag serves to maintain sterility of the radiation shielding container 102 during shipping. In one example, a user at the second location may open the sealed sterile bag and employ the sterile radioactive seeds. In another example, the user at the second location may open the sealed sterile bag and place the radiation shielding container 102 into an autoclave to again sterilize the radioactive seeds. The sterile bag in one example comprises a bag material offered by Dupont (1007 Market Street, Wilmington, Del. 19898), under the trade identifier Tyvek®. In one example, the radiation shielding container 102 is sealed in a Tyvek® bag. In another example, the radiation shielding container 102 is sealed in a plastic tray with a Tyvek® lid.

The apparatus 100 in one example comprises a plurality of components such as mechanical components. A number of such components can be combined or divided in one example of the apparatus 100. The apparatus 100 in one example comprises any (e.g., horizontal, oblique, or vertical) orientation, with the description and figures herein illustrating one exemplary orientation of the apparatus 100, for explanatory purposes.

The steps or operations described herein are just exemplary. There may be many variations to these steps or operations without departing from the spirit of the invention. For instance, the steps may be performed in a differing order, or steps may be added, deleted, or modified.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An apparatus, comprising:
   a single vial that comprises a vial bottom and a vial cap that connect to enclose one or more radioactive seeds; and
   a radiation shielding container that comprises a bottom portion and a top portion that connect to enclose the vial;
   wherein the radiation shielding container and the vial comprise one or more vents for movement of a sterilant therethrough for sterilization of the one or more radioactive seeds within the vial;
   wherein the radiation shielding container has a first longitudinal axis and the single vial has a second longitudinal axis that is substantially coincident with the first longitudinal axis while the single vial is seated within the radiation shielding container;
   wherein the bottom portion of the radiation shielding container comprises a structure that engages the vial bottom to prevent rotational movement of the vial bottom during removal of the vial cap.

2. The apparatus of claim 1, wherein the radiation shielding container comprises a radiation shielding shell around an internal chamber that houses the vial, wherein the one or more vents of the radiation shielding container comprise one or more tortuous paths through the radiation shielding shell.

3. The apparatus of claim 2, wherein the one or more tortuous paths comprise a first tortuous path through the bottom portion and a second tortuous path through the top portion.

4. The apparatus of claim 2, wherein the one or more tortuous paths comprise one or more bends or turns to prevent a line-of-sight path between the internal chamber and an exterior of the radiation shielding container.

5. The apparatus of claim 2, wherein the one or more tortuous paths comprise an opening size that allows the sterilant into the internal chamber but prevents an exit of one of the one or more radioactive seeds from the internal chamber.

6. The apparatus of claim 1, wherein the one or more vents of the vial comprise a sterile barrier that allows passage of the sterilant into the vial for sterilization of the one or more radioactive seeds within the vial.

7. The apparatus of claim 6, wherein the sterile barrier prevents passage of microbes.

8. The apparatus of claim 6, wherein the sterile barrier comprises a Gore-Tex® vent in the vial cap.

9. The apparatus of claim 1, wherein the bottom portion of the radiation shielding container includes a structure with circumferential inwardly-projecting notches and the bottom of the vial includes outwardly-projecting corners dimensioned to engage with corresponding notches to prevent rotation of the bottom of the vial relative to the bottom portion of the radiation shielding container.

10. The apparatus of claim 9, wherein the vial bottom comprises a plurality of outer faces, wherein the one or more notches receive the vial bottom and abut one or more of the plurality of outer faces to prevent rotational movement of the vial bottom during rotational removal of the vial cap.

11. The apparatus of claim 10, wherein the one or more notches abut the one or more of the plurality of outer faces to allow rotational removal of the vial cap while the vial bottom is secured within the bottom portion of the radiation shielding container.

12. The apparatus of claim 9, wherein the vial bottom comprises a hexagonal shape with six outer faces;
   wherein the circumferential protrusion comprises six notches to receive six corners of the hexagonal shaped vial bottom to prevent rotational movement of the vial bottom during rotational removal of the vial cap.

13. The apparatus of claim 9, wherein the circumferential protrusion is integral with or press fit into the bottom portion of the radiation shielding container.

14. The apparatus of claim 1, wherein the vial comprises a cylindrical inner chamber, wherein a top portion of the cylindrical inner chamber comprises a substantially same diameter as a bottom portion of the cylindrical inner chamber.

15. The apparatus of claim 1, wherein the vial is made of a material that can be autoclaved and maintain structural integrity.

16. The apparatus of claim 15, wherein the material of the vial comprises polycarbonate, anti-static plastic, or glass.

17. The apparatus of claim 1, wherein the radiation shielding container is made of stainless steel.

18. The apparatus of claim 1, wherein radiation shielding container comprises a shipping container for the vial of the one or more radioactive seeds.

19. The apparatus of claim 1, further comprising a sterile bag;
   wherein the radiation shielding container is sterilized and sealed in the sterile bag to maintain sterility of the radiation shielding container during shipping.

20. An apparatus, comprising:
   a single vial that comprises a vial bottom and a vial cap that connect to enclose one or more radioactive seeds; and
   a radiation shielding container that comprises a bottom portion and a top portion that connect to enclose the vial;
   wherein the radiation shielding container has a first longitudinal axis and the single vial has a second longitudinal axis that is substantially coincident with the first longitudinal axis while the single vial is seated within the radiation shielding container;
   wherein the radiation shielding container comprises one or more tortuous paths that allow passage of a sterilant and prevent passage of radiation from the one or more radioactive seeds;
   wherein the vial comprises a sterile barrier that allows passage of the sterilant into the vial for sterilization of the one or more radioactive seeds within the vial;
   wherein the bottom portion of the radiation shielding container comprises a structure that engages the vial bottom to prevent rotational movement of the vial bottom during rotational removal of the vial cap.

21. The apparatus of claim 20, wherein the vial bottom comprises a plurality of outer faces, wherein the bottom portion of the radiation shielding container comprises a circumferential protrusion with one or more notches;
   wherein the one or more notches receive the vial bottom and abut one or more of the plurality of faces to prevent rotational movement of the vial bottom during rotational removal of the vial cap.

22. The apparatus of claim 21, wherein the vial bottom comprises a hexagonal shape with six outer faces;
   wherein the circumferential protrusion comprises six notches to receive six corners of the hexagonal shaped vial bottom to prevent rotational movement of the vial bottom during rotational removal of the vial cap.

23. The apparatus of claim 20, wherein the sterile barrier comprises a Gore-Tex vent in the vial cap, wherein the Gore-Tex vent prevents passage of microbes into the vial to maintain sterility of the one or more radioactive seeds within the vial.

24. The apparatus of claim 20, wherein the vial is made of a material that can be autoclaved and maintain structural integrity.

25. The apparatus of claim 20, wherein the radiation shielding container comprises a radiation shielding shell around an internal chamber that houses the vial;
   wherein the one or more tortuous paths comprise one or more bends or turns through the radiation shielding shell to prevent a line-of-sight path between the internal chamber and an exterior of the radiation shielding container.

26. The apparatus of claim 20, wherein the vial comprises a cylindrical inner chamber, wherein a top portion of the cylindrical inner chamber comprises a substantially same diameter as a bottom portion of the cylindrical inner chamber.

27. An apparatus, comprising:
   a single vial that comprises a vial bottom and a vial cap that connect to enclose one or more radioactive seeds;
   means for housing the vial that shields a user from radiation emitted by the one or more radioactive seeds;
   the housing means having a first longitudinal axis and the single vial having a second longitudinal axis that is substantially coincident with the first longitudinal axis while the single vial is seated within the housing means;
   means for allowing passage of a sterilant into the means for housing;
   means for allowing passage of the sterilant into the vial for sterilization of the one or more radioactive seeds within the vial; and
   means for engaging the vial bottom to prevent rotational movement of the vial bottom during removal of the vial cap.

28. The apparatus of claim 27, wherein the vial bottom comprises a plurality of outer faces;
   wherein the means for engaging the vial bottom to prevent rotational movement of the vial bottom during removal of the vial cap comprises means for abutting one or more of the plurality of faces to prevent rotational movement of the vial bottom during rotational removal of the vial cap.

29. The apparatus of claim 27, wherein the means for allowing passage of the sterilant into the vial for sterilization of the one or more radioactive seeds within the vial comprises means for preventing passage of microbes into the vial to maintain sterility of the one or more radioactive seeds within the vial.

30. The apparatus of claim 27, further comprising:
   means for maintaining sterility of the radiation shielding container and the one or more radioactive seeds during shipping of the radiation shielding container.

* * * * *